United States Patent [19]

Gabbay

[11] Patent Number: 4,703,752
[45] Date of Patent: Nov. 3, 1987

[54] CONTRACEPTIVE DEVICE

[76] Inventor: Shlomo Gabbay, 1 Randall Dr., Short Hills, N.J. 07078

[21] Appl. No.: 890,070

[22] Filed: Jul. 24, 1986

Related U.S. Application Data

[63] Continuation-in-part of Ser. No. 768,866, Aug. 23, 1985.

[51] Int. Cl.[4] .............................................. A61F 5/46
[52] U.S. Cl. ...................................... 128/131; 128/127
[58] Field of Search ................................. 128/127–131

[56]  References Cited

U.S. PATENT DOCUMENTS

| 2,310,564 | 2/1943 | Younkins | 128/127 |
| 2,580,133 | 12/1951 | Sheen | 128/127 |
| 2,818,064 | 12/1957 | Leff | 128/127 |
| 3,261,353 | 7/1966 | Johnson | 128/127 |
| 3,371,664 | 3/1968 | Pleshette | 128/127 |
| 4,381,771 | 5/1983 | Gabbay | 128/127 X |
| 4,393,871 | 7/1983 | Vorhauer et al. | 128/127 X |

FOREIGN PATENT DOCUMENTS 0337606  4/1904  France ................................. 128/127

Primary Examiner—Robert A. Hafer
Assistant Examiner—Kathleen J. D'Arrigo
Attorney, Agent, or Firm—Jordan B. Bierman

[57]  ABSTRACT

A contraceptive device for females comprising a toroidal collar having an anterior portion, a posterior portion, an internal wall, and an external wall, the internal wall having an internal diameter sufficient to surround the cervix and the external wall having an outside diameter such that the anterior and posterior fornices are substantially filled by the collar. The posterior portion is in the posterior fornix and the anterior portion is in the anterior fornix. There is a bowl, below the cervix, on the collar and extending downwardly therefrom. A valve depends from the lower portion of the bowl and is connected therewith, thereby to allow flow from said bowl into the vagina but restricting or preventing entry into the bowl from the vagina. A projection is attached to the collar or the bowl extending anteriorly of the device, whereby reversal of the device and/or substantial rotation thereof around the cervix is prevented. It also assists in removal thereof. The projection may be a loop, preferably having thickened sides to aid in preventing unwanted movement of the device after insertion.

92 Claims, 6 Drawing Figures

CONTRACEPTIVE DEVICE

This application is a continuation-in-part of Ser. No. 768,866 filed Aug. 23, 1985.

The present invention is directed to an improved female contraceptive device, more specifically to a device which can be inserted over the cervix and removed at will by the user.

There are a number of types of contraceptive devices which have been generally known. There is a sponge, usually impregnated with a spermicide, which is inserted into the vagina. This has a number of serious disadvantages. In the first place, it does not constitute any form of physical barrier, the sperm may move past it, especially if it is not precisely in the proper position. Furthermore, its action is substantially dependent upon the effectiveness of the spermicide which, especially if the user does not impregnate it properly, may permit at least some sperm to pass. In addition, because the surface of the sponge is porous, any attempt to leave the sponge in the body for an extended period of time is likely to result in serious infection.

Another class of contraceptive devices is the cervical cap. Most prior devices of this kind adhere to the cervix by suction and/or by constriction. However, insertion and removal is difficult and is usually carried out by a physician. Moreover, they cannot be permitted to remain for any extended period of time, because degeneration of the cervix will take place because of the constriction. Furthermore, they cannot remain in place during menstruation because they do not permit any flow through them.

In my U.S. Pat. No. 4,381,771 (issued May 3, 1983) a basic device similar to that of the present invention is disclosed and that disclosure is incorporated herein by reference. The present invention constitutes an improvement thereon.

It is among the objects of the present invention to provide a contraceptive device which can be inserted and removed by the user without the assistance of a health professional.

It is further among the objects of this invention to provide a contraceptive device which can remain in the body indefinitely without risk of infection.

It is still further among the objects of this invention to provide a contraceptive device which cannot be improperly inserted and which will remain in proper position regardless of the body movements.

It is also among the objects of this invention to provide a contraceptive device which will permit flow of secrections out of the uterus, but not permit entry of sperm.

In practicing the present invention to achieve the foregoing objects, there is provided a generally toroidal collar having an anterior portion and a posterior portion, as well as an internal wall and an external wall. The internal wall has a diameter such that it will surround the cervix and preferably exert little or no pressure thereon. The external wall is so constructed that the collar substantially fills the anterior and posterior fornices. The posterior portion of the collar fits into the posterior fornix and the anterior portion fits into the anterior fornix.

There is a bowl, which is located below the cervix when the device is in operative position, on the collar and extending downwardly therefrom. At or adjacent to its lowest point, an opening is provided. The opening leads to a valve which depends from the lower portion of the bowl. The valve allows flow from the bowl into the vagina, but restricts or prevents entry of any substance (including sperm) into the bowl from the vagina.

It is preferable that the valve comprise a pair of cusps extending anteriorly and downwardly from the bowl into the vagina. These cusps are biased toward one another so that, unless there is pressure from the direction of the bowl, the passage therebetween is closed. The cusps should be relatively short compared to their width. It is preferable that the length be less than 1½ times the width and most preferable that it be approximately equal to the width. In a particularly preferred form of the device, the first or upper cusp is extended and sealed to the loop. It is also desirable to make the upper cusp more rigid than the lower cusp, as by thickening. A further feature of the invention is the provision of stiffer, thickened edges at the line at which the upper and lower cusps join one another. These expedients aid in avoiding prolapsing of the valve.

The device of the present invention is provided with a projection which is attached to the collar or the bowl and extends anteriorly of the device. In a preferred embodiment, the projection is a loop of such size that a finger may be inserted therein. For best results, the sides of the loop are thicker than the remainder; horizontally, vertically, or both.

The projection insures that the device will be properly oriented (as between the anterior and posterior portions) when inserted into the body. Second, once inserted, the projection and thickened sides prevent inadvertent rotation of the device around the cervix. Third, the loop allows the user to insert a finger and remove the device without the aid of a health care professional. Fourth, the thickened sides both aid in bearing against the inner wall of the vagina, and also provide a greater area of contact therewith. This gives the user excellent control and the location of the device can be determined by feel. Finally, the device does not bear against the pubic bone, nor does it press on the urethra, as some prior art devices do.

In a particularly advantageous form of the device, a pouch is provided between the bowl and the valve. The pouch is desirably located adjacent the lower portion of the bowl. For best results, it should be relatively soft as compared to the bowl. As a result, the natural pumping action of the vagina will aid in urging the flow of any secretions out through the valve.

In another particularly advantageous form of the device, a flange extends downwardly (and preferably outwardly) from a circle adjacent the opening. As a result, the normal pressure of the inner walls of the vagina will urge the soft underside of the pouch against the flange and thereby seal the valve against any inward flow. When the pressure within the bowl exceeds that exerted by the vagina walls, flow is permitted outwardly. This prevents the introduction of any semen and/or air into the bowl. Should air get in, there is a tendency to cause the device to release from its position surrounding the cervix.

It has been noted that the vagina expands and contracts during various portions of the normal menstrual cycle. Thus, it is possible that a device in accordance with the present invention would fit satisfactorily at certain times of the month, but be too loose or too tight during others. In order to provide for this, a particularly preferred form of the invention consists of a modification of the loop as described thus far. More specifically, instead of the sides extending substantially straight and parallel with one another, they are each curved outwardly; preferably so as to extend wider than the maximum width of the bowl. This provides the necessary flexibility to maintain the device in its appropriate position at all times.

In the accompanying drawings, constituting a part hereof and which like reference characters indicate like parts, FIG. 1 is a diagramatic view showing the device of the present invention in place;

Figure 1:
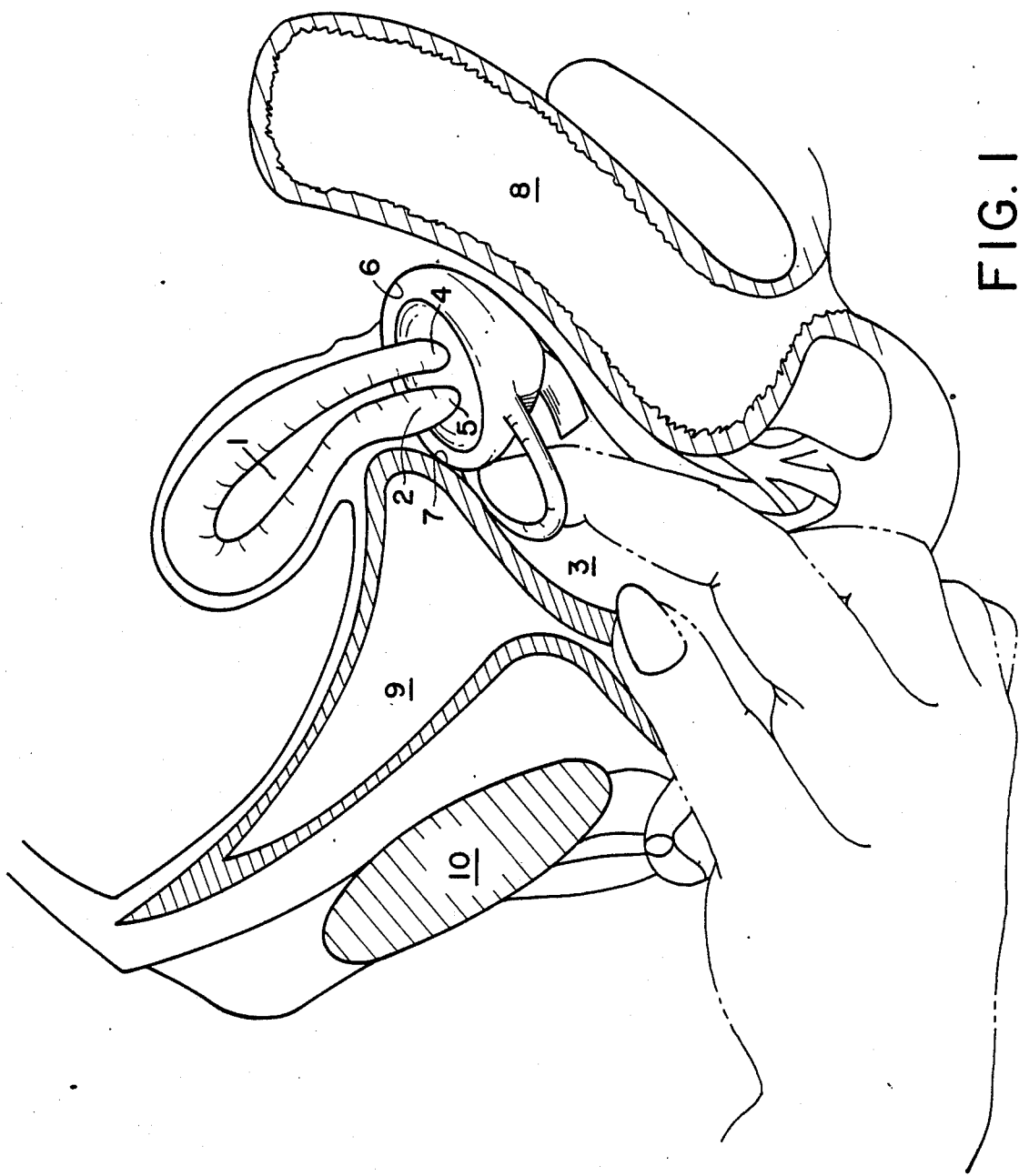

Referring specifically to FIG. 1, uterus 1 has cervix 2 and is located at the upper end of vagina 3. Cervix 2 comprises posterior lip 4 and anterior lip 5. Immediately adjacent the lips are posterior fornix 6 and anterior fornix 7, colon 8 is behind vagina 3 and bladder 9 is in front. Pelvic bone 10 is also shown.

Figure 2:
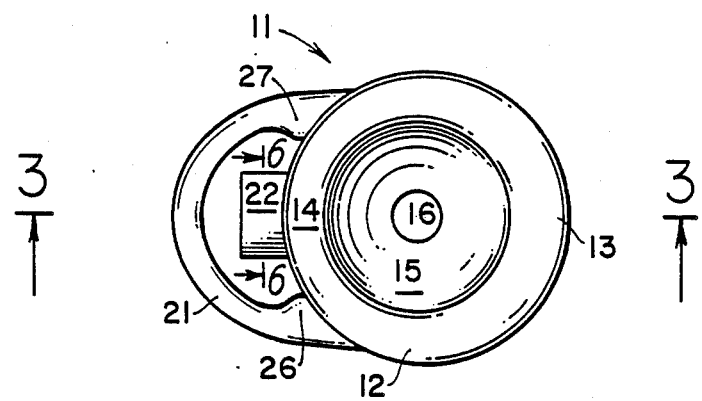
FIG. 2 is a plan view of the device.
Figure 3:
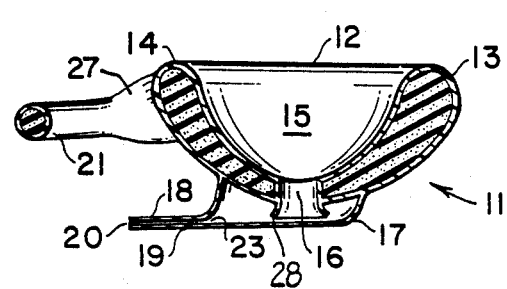
FIG. 3 is a sectional view of the device along line 3—3 of FIG. 2.

As can best be seen in FIG. 2 and 3, the device generally is shown at 11 and comprises collar 12 having posterior portion 13 and anterior portion 14. As can be particularly seen in FIG. 3, anterior portion 14 is smaller in cross section than posterior portion 13. This is to conform to the normal difference in size between anterior fornix 7 and posterior fornix 6. Bowl 15 extends downwardly from collar 12 and has opening 16 at the bottom thereof. This leads into pouch 17 which, in turn, leads to valve 22.

Valve 22 is connected to pouch 17 at end 23. Cusps 18 and 19 are biased together and valve 22 ends at outlet 20. In a preferred form of the device, first cusp 18 carries extension 24 which is affixed to loop 21. This effectively prevents prolapsing of valve 22 and restrains it from folding back on itself. In another preferred form of the device, loop 21 is provided with sides 26 and 27 which are horizontally and/or vertically thicker than other portions of loop 21. Sides 26 and 27 aid in preventing unwanted rotation or other movement of the device about the cervix.

Loop 21 is provided on collar 12 and, as can be seen in FIG. 1, is large enough to receive a finger. Loop 21 prevents improper orientation of device 11 as it can only be inserted with loop 21 projecting anteriorly. Thus, it is impossible to reverse anterior portion 14 and posterior portion 13. In addition, once device 11 is inserted, loop 21 prevents body movements from causing rotation of collar 12 around cervix 2. Finally, as shown in FIG. 1, device 11 may be removed by the user by inserting a finger into loop 21 and pulling device 11 out. Of course, it this last function is deemed to be of less importance than the others, loop 21 can be replaced by a projection.

In another preferred form of the device, flange 28 extends downwardly (and preferably outwardly) from adjacent opening 16. Pouch 17 is relatively thin and flexible so that the natural action of the vagina will urge pouch 17 to seal against flange 28. This prevents any backflow from the vagina into bowl 15. At the same time, when the fluid pressure in bowl 15 exceeds that exerted by the vagina on pouch 17, such fluid is permitted to flow out through valve 23. This arrangement is such that the device bears against the walls of the vagina, and does not press upon the pubic bone. The latter is undesirable, since it tends to cause the bone to degrade or deteriorate and also since it exerts pressure on the urethra.

Figure 4:
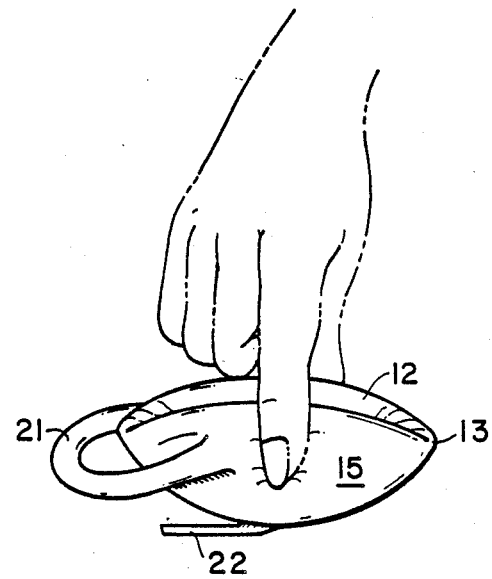
FIG. 4 is a view showing the device being compressed for insertion.
Figure 5:
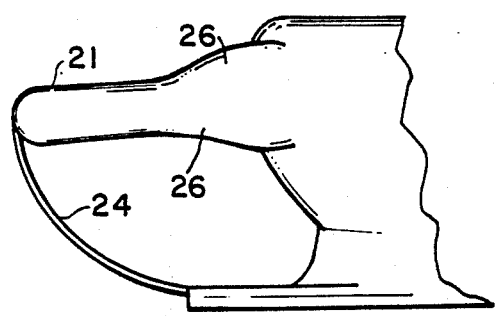
FIG. 5 is a fragmentary view of a preferred form of the device.
Figure 6:
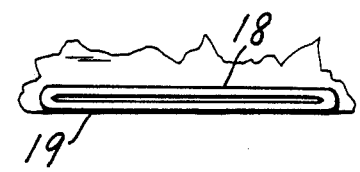
FIG. 6 is a section along line 6—6 of FIG. 2.

To insert the device, it is first compressed as shown in FIG. 4. It is then introduced into vagina 3 and placed over cervix 2. The natural resilience of collar 12 will cause it to assume the shape and position shown in FIG. 1. Since the internal diameter of collar 12 is preferably larger than the diameter of cervix 2, little or no pressure will be exerted thereon. In the most desirable form of the device, the outer diameter of collar 12 is somewhat larger than the inner diameter of vagina 3 adjacent cervix 2. This causes the external portion to bear against the inner wall of the vagina, thereby aiding in holding it in place.

In a modification of the device, the outer diameter of collar 12 is approximately the same size as the inner diameter of vagina 3 adjacent cervix 2, and device 11 is retained in position primarily by a snug fit of the posterior portion 13 and anterior portion 14 in posterior fornix 6 and anterior fornix 7, respectively.

Once inserted, the device can remain in place indefinitely. Any secretions from uterus 1 flow into bowl 15 through opening 16, and into pouch 17. The pressure thereof causes cusps 18 and 19 to separate and permit the secretions to flow through valve 22 and to exit at outlet 20.

A further modification of the device is shown in FIG. 2. Sides 26 and 27 of loop 21 are curved outwardly so that they preferably extend beyond the width of collar 12. This gives them sufficient flexibility so that they are capable of bearing against the walls of the vagina even when it is enlarged during the menstrual cycle.

The device is manufactured with a smooth, impervious surface so that there is no opportunity for any secretions or microorganisms to adhere thereto. The device may advantageously be made of foam rubber, covered with an impervious outer layer. This layer is made of a material which is compatible with the human body and one to which semen does not readily adhere; e.g. the clean medical grade of "silastic", manufactured by Dow Corning.

In a modification of the device, the loop or projection should angle downwardly as it extends anteriorly. It has been found that this will facilitate the use of the device. Also, the cusps of the valve should be sufficiently resilient so that they will snap back into place (extending anteriorly of the device) when the penis is removed. This prevents prolapsing of the valve and consequent inability thereof to function. This can be accomplished by making the cusps relatively short as compared to their width.

It has also been found that it is advantageous to provide a thickened portion along the lines at which the upper and lower cusps are joined. Also, the upper cusp can be thickened. Either or both of these expedients aid in making the cusps resilient so that they will return to their normal position after removal of the penis. This aids in preventing any flow from the vagina into the bowl.

While only a limited number of specific embodiments of the present invention have been expressly disclosed, it is, nonetheless, to be broadly construed and not to be limited except by the character of the claims appended hereto.

I claim:

1. A female contraceptive device comprising a generally toroidal collar having an anaterior portion, a posterior portion, an internal wall, and an external wall, said internal wall having an internal diameter sufficient to surround the cervix and said external wall having an external diameter such that the anterior and posterior fornices are substantially filled by said collar, said posterior portion being in the posterior fornix and said anterior portion being in the anterior fornix, a bowl, below the cervix, on said collar and extending downwardly therefrom, a valve depending from a lower portion of said bowl and being connected therewith, said valve allowing flow from said bowl into the vagina but restricting or preventing entry into said bowl from said vagina, a substantially solid loop adapted to receive a finger and having sides thickened in the lateral direction, said loop attached to said collar and extending anteriorly of said device, the lateral distance between the extremes of said thickened sides being greater than said external diameter, whereby reversal of said device and/or substantial rotation thereof around the cervix is prevented and whereby insertion of a finger will facilitate removal of the device.

2. The device of claim 1 wherein said valve comprises upper and lower cusps extending from said bowl into the vagina and biased together, the upper cusp being stiffer than the lower cusp.

3. The device of claim 2 wherein said loop extends downwardly from said device.

4. The device of claim 2 wherein said upper cusp is thicker than said lower cusp.

5. The device of claim 1 wherein there is a pouch between said bowl and said valve adjacent the lower portion of said bowl.

6. The device of claim 5 wherein said pouch is soft as compared with said bowl whereby the natural pumping action of the vagina urges flow out through said valve.

7. The device of claim 5 wherein said cusps extend from said pouch.

8. The device of claim 1 wherein said valve comprises two cusps extending from said bowl into the vagina and biased together.

9. The device of claim 8 wherein said cusps extend anteriorly of said device.

10. The device of claim 8 wherein the length of said cusps is less than 1½ times their width.

11. The device of claim 10 wherein the length of said cusps is approximately equal to their width.

12. The device of claim 8 wherein said cusps are softer than said bowl.

13. The device of claim 8 wherein said valve is connected to said loop by an extension, whereby the tendency of said valve to prolapse is reduced.

14. The device of claim 13 wherein said cusps comprise an upper cusp and a lower cusp, said upper cusp being connected to said loop by said extension.

15. The device of claim 1 wherein said posterior portion is larger in cross section than said anterior portion.

16. The device of claim 1 wherein said external diameter is at least as large as the internal diameter of the vagina adjacent the cervix whereby said collar is held in place at least partly by pressure of said external wall against the internal wall of the vagina.

17. The device of claim 1 wherein said external diameter is larger than the internal diameter of the vagina adjacent the cervix.

18. The device of claim 1 wherein said sides are vertically thickened.

19. The device of claim 1 wherein said valve is connected to said loop by an extension, whereby the tendency of said valve to prolapse is reduced.

20. The device of claim 1 wherein said sides are horizontally thickened.

21. The device of claim 1 wherein said sides are vertically thickened.

22. The device of claim 21 wherein said sides are horizontally thickened.

23. The device of claim 1 wherein said cusps are joined to each other at edges, said edges being stiffer than said lower cusp.

24. A female contraceptive device comprising a generally toroidal collar having an anaterior portion, a posterior portion, an internal wall, and an external wall, said internal wall having an internal diameter sufficient to surround the cervix and said external wall having an external diameter such that the anterior and posterior fornices are substantially filled by said collar, said posterior portion being in the posterior fornix and said anterior portion being in the anterior fornix, a bowl, below the cervix, on said collar and extending downwardly therefrom, a valve depending from a lower portion of said bowl and being connected therewith, said valve allowing flow from said bowl into the vagina but restricting or preventing entry into said bowl from said vagina, a substantially solid loop adapted to receive a finger and having sides thickened in the lateral direction, said loop attached to said bowl and extending anteriorly of said device, the lateral distance between the extremes of said thickened sides be greater than said external diameter, whereby reversal of said device and/or substantial rotation thereof around the cervix is prevented and whereby insertion of a finger will facilitate removal of the device.

25. The device of claim 24 wherein said valve comprises upper and lower cusps extending from said bowl into the vagina and biased together, the upper cusp being stiffer than the lower cusp.

26. The device of claim 25 wherein said loop extends downwardly from said device.

27. The device of claim 25 wherein said upper cusp is thicker than said lower cusp.

28. The device of claim 24 wherein there is a pouch between said bowl and said valve adjacent the lower portion of said bowl.

29. The device of claim 28 wherein said pouch is soft as compared with said bowl whereby the natural pumping action of the vagina urges flow out through said valve.

30. The device of claim 28 wherein said cusps extend from said pouch.

31. The device of claim 24 wherein said valve comprises two cusps extending from said bowl into the vagina and biased together.

32. The device of claim 31 wherein said cusps extend anteriorly of said device.

33. The device of claim 31 wherein the length of said cusps is less than 1½ times their width.

34. The device of claim 33 wherein the length of said cusps is approximately equal to their width.

35. The device of claim 31 wherein said cusps are softer than said bowl.

36. The device of claim 24 wherein said posterior portion is larger in cross section than said anterior portion.

37. The device of claim 24 wherein said external diameter is at least as large as the internal diameter of the vagina adjacent the cervix whereby said collar is held in place at least partly by pressure of said external wall against the internal wall of the vagina.

38. The device of claim 37 wherein said external diameter is larger than the internal diameter of the vagina adjacent the cervix.

39. The device of claim 24 wherein said sides are vertically thickened.

40. A female contraceptive device comprising a generally toroidal collar having an anaterior portion, a posterior portion, an internal wall, and an external wall, said internal wall having an internal diameter sufficient to surround the cervix and said external wall having an external diameter such that the anterior and posterior fornices are substantially filled by said collar, said posterior portion being in the posterior fornix and said anterior portion being in the anterior fornix, a bowl, below the cervix, on said collar and extending downwardly therefrom, a valve depending from a lower portion of said bowl and being connected therewith, said valve allowing flow from said bowl into the vagina but restricting or preventing entry into said bowl from said vagina, a projection attached to said collar or said bowl and extending anteriorly of said device, an opening in aid bowl connecting with said valve, a circumferential flange extending downwardly into said valve from adjacent said opening, whereby said valve is adapted to seal against said flange when the pressure in the vagina is greater than the internal pressure in said bowl.

41. A female contraceptive device comprising a generally toroidal collar having an anaterior portion, a posterior portion, an internal wall, and an external wall, said internal wall having an internal diameter sufficient to surround the cervix and said external wall having an external diameter such that the anterior and posterior fornices are substantially filled by said collar, said posterior portion being in the posterior fornix and said anterior portion being in the anterior fornix, a bowl, below the cervix, on said collar and extending downwardly therefrom, a valve depending from a lower portion of said bowl and being connected therewith, said valve allowing flow from said bowl into the vagina but restricting or preventing entry into said bowl from said vagina, a loop attached to said collar extending anteriorly of said device and adapted to receive a finger, said loop comprising a pair of sides extending from said collar laterally beyond said external diameter.

42. The device of claim 41 wherein there is a pouch between said bowl and said valve adjacent the lower portion of said bowl.

43. The device of claim 41 wherein said pouch is soft as compared with said bowl whereby the natural pumping action of the vagina urges flow out through said valve.

44. The device of claim 41 wherein said valve comprises two cusps extending from said bowl into the vagina and biased together.

45. The device of claim 44 wherein said valve is connected to said loop by an extension, whereby the tendency of said valve to prolapse is reduced.

46. The device of claim 45 wherein said cusps comprise an upper cusp and a lower cusp, said upper cusp being connected to said loop by said extension.

47. The device of claim 41 wherein said cusps extend anteriorly of said device.

48. The device of claim 41 wherein said cusps extend from said pouch.

49. The device of claim 41 wherein said cusps are softer than said bowl.

50. The device of claim 41 wherein said loop extends downwardly from said device.

51. The device of claim 41 wherein said posterior portion is larger in cross section than said anterior portion.

52. The device of claim 41 wherein said external diameter is at least as large as the internal diameter of the vagina adjacent the cervix whereby said collar is held in place at least partly by pressure of said external wall against the internal wall of the vagina.

53. The device of claim 52 wherein said external diameter is larger than the internal diameter of the vagina adjacent the cervix.

54. The device of claim 41 wherein said upper cusp is stiffer than said lower cusp.

55. The device of claim 54 wherein said cusps are joined to each other at edges, said edges being thicker than said lower cusp.

56. The device of claim 41 wherein said valve is connected to said loop by an extension, whereby the tendency of said valve to prolapse is reduced.

57. A female contraceptive device comprising a generally toroidal collar having an anaterior portion, a posterior portion, an internal wall, and an external wall, said internal wall having an internal diameter sufficient to surround the cervix and said external wall having an external diameter such that the anterior and posterior fornices are substantially filled by said collar, said posterior portion being in the posterior fornix and said anterior portion being in the anterior fornix, a bowl, below the cervix, on said collar and extending downwardly therefrom, a valve depending from a lower portion of said bowl and being connected therewith, said valve allowing flow from said bowl into the vagina but restricting or preventing entry into said bowl from said vagina, a loop attached to said bowl extending anteriorly of said device and adapted to receive a finger, said loop comprising a pair of sides extending from said bowl laterally beyond said external diameter.

58. The device of claim 57 wherein there is a pouch between said bowl and said valve adjacent the lower portion of said bowl.

59. The device of claim 57 wherein said pouch is soft as compared with said bowl whereby the natural pumping action of the vagina urges flow out through said valve.

60. The device of claim 57 wherein said valve comprises two cusps extending from said bowl into the vagina and biased together.

61. The device of claim 60 wherein said valve is connected to said loop by an extension, whereby the tendency of said valve to prolapse is reduced.

62. The device of claim 61 wherein said cusps comprise an upper cusp and a lower cusp, said upper cusp being connected to said loop by said extension.

63. The device of claim 57 wherein said cusps extend anteriorly of said device.

64. The device of claim 57 wherein said cusps extend from said pouch.

65. The device of claim 57 wherein said cusps are softer then said bowl.

66. The device of claim 57 wherein said loop extends downwardly from said device.

67. The device of claim 57 wherein said posterior portion is larger in cross section than said anterior portion.

68. The device of claim 57 wherein said external diameter is at least as large as the internal diameter of the vagina adjacent the cervix whereby said collar is held in place at least partly by pressure of said external wall against the internal wall of the vagina.

69. The device of claim 68 wherein said external diameter is larger than the internal diameter of the vagina adjacent the cervix.

70. The device of claim 57 wherein said upper cusp is stiffer than said lower cusp.

71. The device of claim 70 wherein said cusps are joined to each other at edges, said edges being thicker than said lower cusp.

72. The device of claim 57 wherein said valve is connected to said loop by an extension, whereby the tendency of said valve to prolapse is reduced.

73. The device of claim 40 wherein said flange extends

74. The device of claim 40 wherein said projection is a loop.

75. The device of claim 74 wherein said loop extends downwardly from said device.

76. The device of claim 74 wherein said sides extend outwardly beyond said collar and said bowl.

77. The device of claim 40 wherein said valve comprises upper and lower cusps extending from said bowl into the vagina and biased together, the upper cusp being stiffer than the lower cusp.

78. The device of claim 77 wherein said upper cusp is thicker than said lower cusp.

79. The device of claim 40 wherein there is a pouch between said bowl and said valve adjacent the lower portion of said bowl.

80. The device of claim 79 wherein said pouch is soft as compared with said bowl whereby the natural pumping action of the vagina urges flow out through said valve.

81. The device of claim 79 wherein said cusps extend from said pouch.

82. The device of claim 40 wherein said valve comprises two cusps extending from said bowl into the vagina and biased together.

83. The device of claim 82 wherein said cusps extend anteriorly of said device.

84. The device of claim 82 wherein said cusps are softer than said bowl.

85. The device of claim 82 wherein said valve is connected to said loop by an extension, whereby the tendency of said valve to prolapse is reduced.

86. The device of claim 85 wherein said cusps comprise an upper cusp and a lower cusp, said upper cusp being connected to said loop by said extension.

87. The device of claim 40 wherein said posterior portion is larger in cross section than said anterior portion.

88. The device of claim 40 wherein said external diameter is at least as large as the internal diameter of the vagina adjacent the cervix whereby said collar is held in place at least partly by pressure of said external wall against the internal wall of the vagina.

89. The device of claim 88 wherein said external diameter is larger than the internal diameter of the vagina adjacent the cervix.

90. The device of claim 88 wherein said external diameter is larger than the internal diameter of the vagina adjacent the cervix.

91. The device of claim 40 wherein said valve is connected to said loop by an extension, whereby the tendency of said valve to prolapse is reduced.

92. The device of claim 40 wherein said sides are thickened.

* * * * *

UNITED STATES PATENT AND TRADEMARK OFFICE

(12)         CERTIFICATE EXTENDING PATENT TERM
UNDER 35 U.S.C. § 156

| | | | |
|---|---|---|---|
| (68) | PATENT NO. | : | 4,703,752 |
| (45) | ISSUED | : | November 3, 1987 |
| (75) | INVENTOR | : | Shlomo Gabbay |
| (73) | PATENT OWNER | : | Shlomo Gabbay |
| (95) | PRODUCT | : | Lea's Shield® |

This is to certify that an application under 35 U.S.C. § 156 has been filed in the United States Patent and Trademark Office, requesting extension of the term of U.S. Patent No. 4,703,752 based upon the regulatory review of the product Lea's Shield® by the Food and Drug Administration. Since it appears that the requirements of the law have been met, this certificate extends the term of the patent for the period of

(94)                  Five years from August 23, 2005, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 9th day of February 2006.

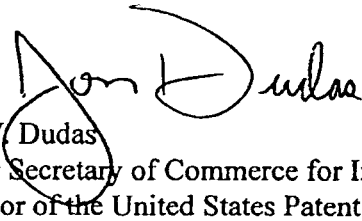

Jon W. Dudas
Under Secretary of Commerce for Intellectual Property and Director of the United States Patent and Trademark Office